(12) United States Patent
Smith

(10) Patent No.: US 8,597,894 B2
(45) Date of Patent: Dec. 3, 2013

(54) DETERMINING IMMUNOGLOBULINS IN NON-BLOOD BODY FLUIDS OF NEONATAL UNGULATES

(75) Inventor: Nathan L. Smith, North Andover, MA (US)

(73) Assignee: Cytosignet, Inc., North Andover, MA (US)

( * ) Notice: Subject to any disclaimer, the term of this patent is extended or adjusted under 35 U.S.C. 154(b) by 445 days.

(21) Appl. No.: 12/610,649

(22) Filed: Nov. 2, 2009

(65) Prior Publication Data

US 2010/0111934 A1    May 6, 2010

Related U.S. Application Data

(60) Provisional application No. 61/110,759, filed on Nov. 3, 2008.

(51) Int. Cl.
*G01N 33/53* (2006.01)

(52) U.S. Cl.
USPC ............................................. 435/7.1; 435/7.2

(58) Field of Classification Search
None
See application file for complete search history.

(56) References Cited

U.S. PATENT DOCUMENTS

| | | |
|---|---|---|
| 2001/0018220 A1 | 8/2001 | McVicker et al. |
| 2005/0208608 A1 | 9/2005 | Raven et al. |

FOREIGN PATENT DOCUMENTS

EP    0170494 A2    2/1986

OTHER PUBLICATIONS

Yokomizo et al. (Vet. Immu. & Immunopathology 2002 vol. 87, p. 291-300).*
Hurlimann et al. (Immunology 1971, vol. 21, p. 101-111).*
Mach et al.; IgA with "Secretory Piece" in Bovine Colstrum and Saliva; Nature, Aug. 30, 1969, vol. 223; pp. 952-955.
Saif et al.; Enteric Viral Invections of Calves and Passive Immunity; J. Dairy Sci., 1985, vol. 68; pp. 206-228.
Atsuko Toyoguchi, et al. Antibody Reactivity to *Cryptosporidium parvum* in Saliva of Calves after Experimental Infection (2001) Journal of Veterinary Medical Science, vol. 62(11): 1231-1234.
Toyoguchi, A., et al., Specific IgA Antibody Response to Coproantigens of *Cryptosporidum parvum* in Serum and Saliva of Calves After Experimental Infection, Veterinary Parasitology, Apr. 1, 2001, vol. 96, No. 3, pp. 213-220.
Mach, Jean-Pierre, et al., Secretory IgA, A Major Immunoglobulin in Most Bovine External Secretions, Journal of Immunology, Jan. 1, 1971, vol. 106, No. 2, pp. 552-563.

* cited by examiner

*Primary Examiner* — Jacob Cheu
(74) *Attorney, Agent, or Firm* — Hodgson Russ LLP

(57) ABSTRACT

Provided is a method for determining immunoglobulins in a neonatal ungulate. The method entails obtaining a sample of oral secretions from the neonatal ungulate and measuring an amount of immunoglobulins in the sample of oral secretions. The method is faster and more convenient than previously available methods for determining immunglobulins in neonatal ungulates, such as neonatal horses and cattle.

13 Claims, 1 Drawing Sheet

DETERMINING IMMUNOGLOBULINS IN NON-BLOOD BODY FLUIDS OF NEONATAL UNGULATES

This application claims priority to U.S. provisional application No. 61/110,759, filed on Nov. 3, 2008, the entire disclosure of which is incorporated herein by reference.

FIELD OF THE INVENTION

This invention relates generally to determining immunoglobulins in body fluids other than blood from neonatal ungulates, and more specifically to determining immunoglobulins in oral fluid obtained from neonatal ungulates.

BACKGROUND OF THE INVENTION

Immunoglobulins (antibodies) are necessary to defend against infection, poisoning, and other potential threats to the health and wellbeing of vertebrates. The presence of immunoglobulins at the interface of a vertebrate organism and the outside environment is the front line of the defense system. Examples of such interfaces include, but are not limited to, the oral cavity and the rest of the digestive system, the nasal cavities and associated respiratory system, the urogenital system, and the eyes. In these structures, antibodies are present in mucosal and other secretions.

Embryonic vertebrates are immunologically naïve. Connor et al (Conner, G. H., M. Richardson, et al. (1977) "Immune responses of the bovine fetus" *J Dairy Sci* 60(2): 289-93) report that ungulates, calves and lambs, are capable of an immune response when challenged by in utero vaccination. In the absence of such direct challenge by antigens in the sterile uterine environment, fetal ungulates produce no antibodies. In order to survive, therefore, various mechanisms have evolved to provide new born animals with antibodies to protect them after birth, said mechanisms usually involve passively transferring maternal antibodies to the offspring. In placental mammals, classified in the taxon Eutheria, the method of transfer of antibody to the offspring is dependent upon the interface between the placental and the uterine tissues. For example, the hemochorial placentae of primates and rodents allow for passage of immunoglobulins across the placenta to the embryo in utero. At birth antibody protection is present. In animals with endotheliochorial placental interface, such as dogs and cats, limited prenatal immunoglobulin passage occurs through the placenta and must be supplemented by antibody transferred to the neonate after birth. In epitheliochorial placental animals, such as cattle, pigs, horses, deer, and a vast number of related species, no transplacental transfer of immunoglobulin occurs and all antibody protection must be acquired by the neonate after birth.

The primary mechanism of postnatal passive transfer of immunity is neonatal ingestion of colostrum, the "first milk", shortly after birth. This fluid is produced by the mammary glands before parturition and is extremely high in immunoglobulins. Upon ingesting colostrum, immunoglobulins are absorbed from the neonatal gut and transferred into the circulatory system wherein they function as antibodies in the nascent immune system. In species that depend upon passive transfer of immunoglobulin antibodies from colostrum, such transfer only occurs for a relatively short time, typically about 12-36 hours, during which time the intestine is permeable. After that time, transfer of immunoglobulins does not occur and, therefore, additional passive transfer of immunity from any ingested materials becomes impossible. This mechanism of preparing the newborn for life outside of the uterus is found in a large and ubiquitous group of mammals known as ungulates.

Ungulates are generally hoofed mammals but include some modern species which have hoofed ancestors. Ungulate species include many domesticated animals such as cattle, goats, sheep, horses, and swine as well as non-domesticated animals used as human food such as deer, antelopes, whales, etc. Ungulates have epitheliochorial placentae, vide supra, and, therefore, depend upon postnatal passive transfer of immunity. In regard to passive transfer of immunity to offspring, the placental structure and prenatal function dictates a high degree of similarity among ungulate species in contrast to other mammalian species with different placental-uterine interface structures.

Ungulate immunology is similar to that of other mammals with immunoglobulin classes or isotypes IgG, IgM, serum IgA, and IgE (Cruse, J. M. and R. E. Lewis (2002) *Illustrated Dictionary of Immunology*, CRC Press). Immunoglobulin G isotypes of $IgG_1$ and $IgG_2$ are present in ungulate serum. Similar to other mammalian species, IgA predominates at mucosal surfaces. Cruse and Lewis (ibid) also report that products of the preparturient ruminant mammary gland are "different in immunoglobulin content compared to other species." Colostrum contains a high concentration of IgG and lower concentrations of IgM and IgA. Therefore, immunity is afforded to the neonatal ungulate primarily by IgG and usually of one isotype. For example, in the bovine, $IgG_1$ is the predominant immunoglobulin in colostrum and, therefore, in the circulation of the calf after successful passive transfer of immunity.

Failure of passive transfer (FPT) of immunity is a potentially life-threatening condition to the neonate. FPT may occur due to a number of causes alone or in combination including: inadequate supply of colostrum, low quality colostrum, failure of the neonate to suckle, failure to absorb ingested immunoglobulins from the gut, metabolic breakdown of the antibodies in the neonate, and others. Those skilled in the art are well aware of the danger of FPT to neonatal animals and have developed procedures, practices, tests, and remedies to prevent, detect, or counter the risk. Despite awareness and various procedures, FPT remains a significant problem in raising livestock and other animals around the world. For example, package inserts accompanying FPT testing products, VMRD (VMRD, Inc. P.O. Box 502, Pullman, Wash. 99163, U.S.A.) teach that more than 10% and up to 40% of dairy and beef calves fail to absorb adequate levels of immunoglobulins.

Passive transfer of immunity occurs along a continuum from no transfer to acceptable transfer of antibodies and therefore protection from infection for the neonate. The majority of newborn ungulates receive sufficient antibody to be considered normal and to thrive with normal husbandry including that supplied by the dam. At the lower end of the passive transfer continuum are those animals receiving no antibodies that will not survive without intervention. Between these two extremes are those individuals which would benefit from supportive treatment to maximize thrift, i.e., healthy and vigorous growth. The term "failure of passive transfer" or "FPT" describes less than normal or sufficient transfer of antibody to an individual during the first few feeding postpartum. FPT is also sometimes referred to in the art as "partial FPT".

Current practice for detecting FPT is to draw a blood sample within a day or two of birth, depending on the animal species being tested, and determine total protein or immunoglobulin in the sample. If present, the concentration of antibody protein is estimated or measured and compared to levels established as sufficient for successful transfer of immunity for that species. Testing methods include measuring total serum protein by refractometry or precipitation with zinc sulphate and measuring immunoglobulins in the blood by various immunoassay methods such as latex agglutination, radial immunodiffusion (RID), enzyme linked immunosorbant assay (ELISA), lateral flow rapid tests, and others. Blood is drawn to perform these test and in most cases blood cells must be removed prior to performing the test. Thus, existing methods for determining amounts of immunoglobulin in neonatal ungulates are time consuming, labor intensive and require obtaining, transporting and storing blood samples. There is accordingly a need for alternative and improved methods for determining immunoglobulin content in neonatal ungulates.

BRIEF DESCRIPTION OF THE FIGURE

FIG. 1 provides a photographic representation of results of performing one embodiment of the invention using a lateral flow device for immunoglobulin detection. To obtain the results depicted in FIG. 1, oral fluid samples were obtain using conventional techniques and applied to commercially available lateral flow devices depicted in FIG. 1 and as generally described in Example VI. The presence of a visible line at location "C", control, indicates that the test functional. The presence of a line at location "T", as in the top—"Cow"—sample, indicates that the IgG concentration in sample was sufficiently low as to not inhibit the immunoreaction causing the line to form and be visible. The absence of the line at location "T"—as in the two (2) calf samples—indicates that the IgG concentration in the sample inhibited formation of the line. The three devices were run using the same procedure at the same time using respectively different samples.

SUMMARY OF THE INVENTION

The invention provides a method for determining immunoglobulins in a neonatal ungulate comprising obtaining a sample of oral secretions from the neonatal ungulate and measuring an amount of immunoglobulins in the sample of oral secretions. The method permits measuring the amount of any type or sub-type of immunoglobulin. In various non-limiting examples the method can be performed on neonatal members of the family cervidae or members of a genus selected from *Bos, Equus and Sus*. Performance of the method of the invention can identify animals that are candidates for supplementation and/or therapy using compositions comprising immunglobulins, such as animals who may have failure of passive transfer. The invention accordingly provides for administering such compositions to animals identified by the method of the invention as a candidate for the supplementation and/or therapy. The method of the invention can be used over time to monitor the efficacy of such interventions if desired.

DETAILED DESCRIPTION OF THE INVENTION

The invention provides a method for determining immunoglobulins in a neonatal ungulate. The method comprises obtaining a sample of oral secretions from the neonatal ungulate and measuring an amount of immunoglobulins in the sample of oral secretions. Advantages of the present invention include but are not limited to exploiting the speed and efficiency by which collection of oral fluid can be performed, which is less technically demanding and time consuming than drawing blood. Further, oral fluid samples used in the method of the invention can be analyzed with little or no pretreatment. Thus, the invention provides an improved, rapid, and minimally invasive sample collection to facilitate timely and repeated, if necessary, sampling and analysis of immunoglobulin content.

Without intending to be bound by any particular theory, it is considered that the present invention permits detecting antibodies transferred to neonatal ungulates from colostrum ingested shortly after birth, a process known as passive transfer of immunity.

Those skilled in the art will be able to recognize that the method is performed on ungulates that are "neonatal" as it pertains to their age. It is generally considered that a neonatal ungulate is of an age of from immediately after birth until such time as the animal begins producing its own antibodies in amounts sufficient to provide immune protection. Within the context of the invention, a "neonatal" ungulate can be considered to be an ungulate that is of an age from birth and up to 60 days old. Thus, the neonatal ungulate may be from 0-60 days old, including all integers there between. The neonatal ungulate on which the method is performed may also be less than one day old. Accordingly, in various embodiments, the neonatal ungulate may be from 1 and up to 24 hours old, including all integers there between. In various non-limiting embodiments, the neonatal ungulate on which the method of the invention is performed may be no more than 1 hour old, no more than 6 hours old, no more than 12 hours old, or no more than 18 hours old.

It is considered that the method is suitable for use with any terrestrial neonatal ungulate. By "terrestrial" is meant those neonatal ungulates which spend the majority of their lives on land. It is preferable that the method be performed for terrestrial neonatal ungulates that are members of a taxonomical grouping selected from the families Bodivae, Equidae, Cervidae and Suidae. The method can be performed on any neonatal animal from any of these taxonomical groupings, as well as any other neonatal animal that has an epitheliochorial placentae and, therefore, must receive passive transfer of immunity by ingestion.

In particular non-limiting examples with respect to members of Bovidae, the method may be performed on domestic cattle, water buffalo, bison, yak, and antelope. In additional non-limiting embodiments, the method may be performed on neonatal animals belonging to the Order Artiodactyla, such as cattle (Family Bovidae) and Perissodactyla to which horses (Family Equidae) belong. The method can also be performed on any hybrid animal that is obtained via mating of different species that are members of Bovidae, or mating of different species that are members of Equidae, or mating of different species that are members of Cervidae, or mating of different species that are members of Suidae.

In one embodiment, the method is performed on one or more domestic cattle. Those skilled in the art will recognize that domesticated cattle include all breeds of animals that are colloquially referred to as cows, but are most commonly classified collectively as *Bos taurus* or *Bos primigenius*. Thus, any neonatal member of the genus *Bos* may be subjected to the method of the invention.

In particular non-limiting examples with respect to members of the genus *Equus*, the method may be performed on any neonatal member of the family Equidae, which includes but is not necessarily limited to horses, donkeys, and zebras. In one embodiment the method is performed on a neonatal horse. A neonatal horse may be referred to herein as a foal.

In particular non-limiting examples the method may be performed on any neonatal member of the family cervidae, which includes but is not necessarily limited to all varieties of deer, caribou, elk, and moose.

The oral secretions, also referred to herein as oral fluid, can be obtained from the neonatal ungulate using a wide variety of procedures known to those in the art and which include but are not limited to syringing, swabbing, or using of any type of collection vessel, device or technique.

Oral fluid that is used in the method of the invention is produced by ungulates to assist in digesting food, although it also contributes to the immunological defense system of the organism. It is a complex mixture comprising transmucosal exudate in addition to saliva produced by the salivary glands and released into the oral cavity through ducts. Despite multiple sources of secretions, IgA is the primary antibody in various oral fluids from different species and ages constituting about two-thirds of the total immunoglobulins. The total immunoglobulin concentration in oral fluid, however, is typically less than 10% of that in serum.

In one embodiment, the sample of oral fluid used in the method of the invention comprises saliva. In alternative embodiments, the oral fluid can consist essentially of saliva, or consist of saliva, with the proviso that the saliva may contain immunoglobulins. In one embodiment the sample of oral fluid is obtained from the oral cavity of the ungulate.

Immunoglobulins can be measured in the sample of oral secretions obtained from the neonatal ungulate using any of a wide variety of methods, reagents and devices known to those skilled in the art to be suitable for immunoglobulin detection and/or quantification. Suitable techniques and/or devices include but are not limited to ELISA assays, lateral flow cassette formats, dipstick formats, dot blots, Western blotting, Radial Immunodiffusion Testing, or any other suitable techniques. As one non-limiting example, a lateral flow immunoassay device that could be used and/or adapted for use in the method of the invention is described by Newgard et al., *Novel Method for Detecting Bovine Immunoglobulin G in Dried Porcine Plasma as an Indicator of Bovine Plasma Contamination*, J. Agric. Food Chem., 2002. Likewise, U.S. Pat. No. 6,660,534 ("the '534 patent") describes a method of determining the concentration of IgG antibodies in the biological fluids of mammals, which description is hereby incorporated by reference. However, the '534 patent does not contemplate testing oral secretions obtained from a neonatal ungulate because the presence of immunoglobulins in neonatal ungulate oral secretions as disclosed herein for the first time is an unexpected result. Thus, it is only with the benefit of the present disclosure that the suitability of known and commercially available devices, reagents and methods for use in the practicing the invention becomes apparent to those skilled in the art.

The immunoglobulins measured via performance of the present invention can be any immunoglobulins and any immunoglobulin subtypes. In various non-limiting examples the immunoglobulins measured can be total immunoglobulins, or individual immunoglobulin types or subtypes. For example, the immunglobulins could be IgG, IgM, IgA, and/or IgE, or any combination thereof. In one embodiment, the immunoglobulin is IgG. In a particular embodiment, the IgG is $IgG_1$. In one embodiment, $IgG_1$ is measured in oral fluid obtained from a bovine. In other embodiments, the immunoglobulin measured is IgA.

It is considered that the present invention provides valuable information that is useful in assessing passive transfer of immunity. It is also considered that those skilled in the art will recognize from the data presented herein that measuring immunoglobulin content in oral secretions obtained from neonatal ungulates can be correlated with immunoglobulin measurements made from serum obtained from neonatal ungulates. In connection with this, it is known that neonatal calf serum IgG concentrations greater than or equal to 10 mg/ml indicates adequate passive transfer. For example, see Gay C, *Failure of passive transfer of colostral immunoglobulins and neonatal disease in calves: a review*, in Proceedings. Vet Infect Dis Org 1983; 346-364; and, White D G, et al. *Adequate concentration of circulating colostral proteins for market calves*. Vet Rec 1986; 119:112-113. Values less than 10 mg/ml are considered to be indicative of FPT. A widely accepted therapy for FPT in neonatal cattle is to administer two feedings of colostrum or colostrum substitute (50 g IgG/L), one within the first 24 hours of birth and the second 12 hours later. Therefore, in one embodiment, the immunoglobulin amount determined according to the method of the invention can be used for assessing the likelihood that any particular neonatal ungulate has FPT, and/or is a candidate for supplementation or therapy using a composition comprising immunoglobulins.

In one embodiment, an amount of IgG measured in a sample of oral secretions obtained from a neonatal calf can be correlated with the aforementioned parameters that delineate FPT (or adequate passive transfer) such that the neonatal calf from which the sample was obtained is indicated to be a candidate to receive a composition comprising immunogloublins. In this regard, data presented herein demonstrate use of the method of the invention to identify neonatal calf with an abnormal IgG profile wherein the neonatal calf subsequently expired. It is considered that FPT is a likely cause or contributor to the expiration of the calf.

In one embodiment, the amount of immunoglobulins determined by performing the method of the invention can be compared to a control. The control can be any suitable control, examples of which include but are not limited to a standardized curve, an internal control included with the technique and/or device that is used to measure the immunoglobulin amount in the oral fluid, or immunoglobulin amounts measured in samples of oral fluid obtained from animals that were subsequently determined not to be in need of immunoglobulin supplementation, or conversely, from animals that were determined to be in need of such supplementation. If the amount of immunoglobulin in the sample of oral fluid obtained from the animal is less than the amount in the control, it is considered that the animal is a candidate for immunoglobulin supplementation, e.g., a candidate for administering to the animal a composition comprising immunoglobulins. Immunoglobulin supplementation is considered a form of FPT therapy.

In one embodiment, the method of the invention comprises communicating the amount of immunoglobulins determined to be in the sample of oral fluid to an animal health care provider. The animal health care provider can be any individual who can or does administer such a composition comprising immunoglobulins to the animal, or an individual who can recommend or prescribe performance of such a procedure.

In one embodiment, the invention further comprises administering a composition comprising immunoglobulins to a neonatal ungulate that has been determined by performance of the method of the invention to be in need of such supplementation, e.g., the animal has no detectable immunoglobulin of one or any type of immunoglobulin, or the amount of an immunoglobulin measured is determined to be low relative to a control. Methods and compositions for supplementation with a composition comprising immunoglobulins are known.

For example, U.S. Pat. Nos. 5,645,834 and 6,770,278, which are incorporated herein by reference, provide descriptions of some non-limiting examples of suitable compositions and methods for immunoglobulin supplementation.

It will be recognized by those skilled in the art that one novel aspect of the invention is the discovery that antibody content in oral fluid is derived from and related to the antibody concentration in the neonatal blood. This relationship is peculiar to neonatal animals in which the immunoglobulin concentration in the blood varies dramatically depending upon individual circumstances early in life. It is therefore considered that neonatal mammals are immunocompetent, that is capable of producing immunoglobulins, but are immunologically naïve and therefore do not produce immunoglobulins in utero or at the time of or immediately after birth. Without intending to be bound by any particular theory, it is considered that, for this reason, any immunoglobulin present immediately postnatal or within a few days after birth were passively transferred to the neonate from the dam.

It is also considered that the oral cavity is a potential entry point for many pathogens and, therefore, antibodies must be present in the oral cavity to protect the newborn from infection. It is believed based on the findings disclosed herein that the only immunoglobulin available to be secreted into the mouth is that obtained from the dam and is primarily IgG, which is only a minor antibody constituent of adult ungulate oral fluid. These circumstances led to the surprising discovery that passively transferred IgG is rapidly secreted into the mouth in concentrations many times higher than the IgG content of adult oral fluid. Prior to the present invention the art taught that antibodies in milk ingested by neonatal ungulates serve to protect the gastrointestinal tract from infection by pathogenic microorganisms.

One embodiment of the present invention comprises measuring immunoglobulin levels in oral fluid at the time of maximum expected concentration of immunoglobulin in the blood. The time of maximum expected concentration for any particular type of ungulate can be established using conventional techniques that rely on analysis of immunoglobulin content in blood. The time of maximum expected concentration of immunoglobulin in blood is known for some ungulates. For example, current practice is to perform FPT testing in domestic bovines and equines about 24 hours after birth. The present invention has the advantage that collection and processing of oral fluid is less invasive and more convenient than drawing blood. Results thus obtained permit currently used interventions to be undertaken in cases of insufficient transfer of antibodies.

Another embodiment of the invention is to collect oral fluid after feeding or sucking has taken place and while the mechanism of immunoglobulin transfer is active. The invention facilitates providing results in time to treat the newborn, if necessary, by administering a composition that is high in immunoglobulin content by mouth prior to the loss of the ability to transfer ingested immunoglobulin from the gut to the circulatory system.

In another embodiment, the invention facilitates assessing the immune status of the neonatal ungulate by monitoring the immunoglobulin levels during repeated sampling from birth until such time that the young animal has begun producing its own antibodies. In addition to the improved simplicity and convenience of collecting oral fluid compared to blood, the less traumatic sampling is from a site of potential infection and could be repeated as necessary.

It is a further advantage of the present invention that the sample obtained would be compatible with at least several different methods of immunoglobulin detection, both singly on site, i.e. on the farm or in the barn, and in larger batches of multiple samples in the lab. Flexibility as to methods of measurement of immunoglobulin permit the invention to be practiced in various settings such as small farms with a few ruminants giving birth infrequently; zoo and animal parks breeding larger numbers of rare, exotic, and/or endangered species; large-scale commercial food production enterprises with potentially several to many births per day.

The following examples are intended to illustrate particular embodiments of the invention and are not intended to limit the scope of the invention in any way:

EXAMPLE I

Collection of Oral Fluid and Serum Samples from Cows and Calves

Samples were collected from Holstein calves at various times from immediately after birth up to several to several to many days later at the University of New Hampshire (Durham, N.H. 03824 U.S.A.) dairy. Oral fluid was obtained by swabbing the periphery of the mouth outside of the teeth with a 4-inch (10 cm) square cotton gauze pad. The wet gauze was placed into the barrel of a 5 mL syringe which was inserted into a 50 mL conical centrifuge tube and centrifuged for 30 min at 3000 RPM at room temperature. The fluid thus expressed from the pad was aliquoted and frozen at −20 C. Serum samples were obtained by venipuncture, allowed to clot, and serum was separated after centrifugation. Serum samples were stored at −20 C.

EXAMPLE II

Radial Immunodiffusion Testing (SRID) for IgG

Single radial immunodiffusion testing, considered to be the current 'gold standard' method for determining passive transfer of immunity in ungulates, was performed using reagents, standards, apparatus, and protocols obtained from VMRD, Inc., Pullman, Wash., USA. Serum samples collected as described in Example I were tested for IgG concentration in accordance with the manufacturer's instructions. Serum samples obtained from calves before feeding gave no visible precipitin reaction indicating IgG concentrations below the lower limit of detection of the SRID plate beings used. Such results are reported herein as "0" IgG. SRID results using samples collected from calves or cows after feeding are reported herein as the concentration of IgG determined from the standard curve run as recommended by VMRD, Inc. Table 1 summarizes the results obtained with some of these samples. For the data presented in Table 1, the precipitin ring diameter of each sample was measured and compared to the standard curve. IgG concentrations are expressed as mg IgG per mL of serum applied. There is generally a dramatic increase from no measurable IgG at birth to about 10 mg/mL six hours after birth. The IgG concentration increase continues but the increase rate slows until 24 hour at which point the IgG concentration decreases. This decrease is consistent with data shown in subsequent examples that IgG is transported into oral fluid and thereby no longer in the circulatory system.

TABLE 1

Calf Serum SRID Test Results, mg/mL

| | Time Post-Partum, Hrs | | | | |
|---|---|---|---|---|---|
| Animal ID | 0 | 6 | 12 | 24 | 48 |
| Bull 19 | 0 | 14 | 16 | 23 | 13 |
| Bull 20 | 0 | 11 | 24 | 20 | 13 |
| Bull 22 | 0 | 9 | 13 | 12 | 11 |
| Bull 23 | 0 | 10 | 24 | 23 | 19 |
| Bull 29 | 0 | 9 | 19 | 23 | 13 |
| Bull 32 | 0 | 8 | 26 | 21 | 16 |
| Bull 33 | 0 | 13 | 18 | 46 | 18 |

Saliva samples collected as described in Example I were tested in SRID with sensitivity from 50-400 mg/dL with no visible precipitin reaction. These plates were prepared at a low-level sensitivity range compared to 400-3200 mg/dL plates typically used for bovine FPT testing. These negative IgG results found with saliva samples by SRID demonstrated that saliva testing would not be acceptable in current practice of FPT monitoring using SRID devices manufactured for serum testing.

EXAMPLE III

ELISA Testing for Immunoglobulins

ELISA Testing was performed using test reagents, controls, and standards manufactured by Bethyl Laboratories, Inc. Montgomery, Tex. 77356. The tests used were prepared by the manufacturer to be specific for total IgG, IgA, and IgG1. Samples were collected as described in Example I, centrifuged and diluted appropriately to an immunoglobulin concentration within the range of the standard curve for the analyte being detected and measured, and tested in accordance with modification of the manufacturer's instructions wherein cold water fish gelatin was used in the buffers. ELISA testing was performed for immunoglobulins in serum using dilutions recommended by the manufacturer. In addition, saliva testing was specially optimized to increase sensitivity in order to obtain the valid results described herein.

EXAMPLE IV

Detection and Measurement of IgG in Calf Oral Fluid by ELISA

Oral fluid samples obtained as described in Example I were tested by ELISA for IgG concentration. Prior to ingesting colostrum, either suckled from the dam or fed colostrum or colostrum replacer by human attendants, the concentration of IgG was typically less than 20 μg/mL of sample. After feeding, the concentration of IgG in oral fluid was found to be greater than that prior to feeding and most frequently greater than 40 μg/mL. These data indicate that IgG is present in neonatal oral fluid at concentrations sufficiently high to be detected and measured and, therefore, useful in monitoring the transfer of immunity in neonatal animals. In addition, these data indicate that IgG rapidly appears in oral fluid of neonatal calves. This finding is surprising in light of the normal prevalence of IgA in saliva and oral fluid of postneonatal ungulates. Typical results are tabulated in Table 2. To obtain the data presented in Table 2, oral fluid was diluted and tested using ELISA specific for bovine IgG as described in the Examples. The results are expressed as μg IgG per mL of oral fluid with correction applied for the dilution of the samples necessary to perform the assay.

TABLE 2

Oral Fluid IgG ELISA, μg/mL

| | Time Post-Partum, Hrs | | | |
|---|---|---|---|---|
| Animal ID | 0 | 24 | 48 | 216 |
| Heifer 504 | 4 | 134 | | |
| Heifer 505 | 53 | 18 | 41 | 388 |
| Bull 1 | 11 | 137 | | |
| Bull 2 | 195 | 1284 | | |
| Bull 3 | 18 | 80 | | |
| Bull 19 | 11 | 57 | | |
| Bull 20 | 19 | 225 | | |
| Bull 22 | 20 | 41 | | |
| Bull 23 | 42 | 123 | | |
| Bull 29 | 8 | 74 | | |
| Bull 30 | 10 | 43 | | |
| Bull 2 | 11 | 21 | | |
| Bull 33 | 1 | 114 | | |

To obtain the data presented in Table 3, oral fluid was diluted and tested using ELISA specific for bovine IgA as described above. The results are expressed as μg IgA per mL of oral fluid with correction applied for the dilution of the samples necessary to perform the assay. Columns labeled with numbers indicate hours post-partum.

TABLE 3

| Animal ID | 0 | 24 | 48 | 216 |
|---|---|---|---|---|
| Heifer 504 | 37 | 41 | | |
| Heifer 505 | 38 | 29 | 34 | 54 |
| Bull 1 | 34 | 43 | | |
| Bull 2 | 49 | 67 | | |
| Bull 3 | 37 | 51 | | |
| Bull 19 | 14 | 38 | | |
| Bull 20 | 17 | 45 | | |
| Bull 22 | 36 | 35 | | |
| Bull 23 | 34 | 56 | | |
| Bull 29 | 36 | 41 | | |
| Bull 30 | 15 | 36 | | |
| Bull 32 | 44 | 7 | | |
| Bull 33 | 47 | 51 | | |

EXAMPLE V

Detection and Measurement of IgG in a Calf with Insufficient Passive Transfer

Oral fluid sample testing for IgG by ELISA with one calf (No. 505) demonstrated an atypical pattern of IgG concentration (see Table 2). The initial sample, labeled time "0", was taken after the heifer calf had suckled. The concentration of IgG was 53 μg/mL, typical for a post-feeding sample. The sample obtained 24 post-partum was determined to have a concentration of IgG of 16 μg/mL. A decrease in immunoglobulin during the first day is life abnormal and indicates that insufficient passive transfer of immunity may have occurred. An additional sample was collected from the heifer 48 hours after birth at which time the calf was observed to be weak and sickly. The dairy barn manager indicated that between 24 and 30 hours the calf had been given nutrition directly into the stomach using a tube and given other supportive therapy. Calf no. 505 subsequently died. This result clearly indicates that the testing of oral fluid gave results consistent with abnormal passive transfer. In addition, these results indicate the surprising finding that the level IgG secreted in oral fluid of neonates decreases with time in a calf suspected of FPT.

EXAMPLE VI

Detection of IgG in Calf Oral Fluid by Lateral Flow Devices

Lateral flow rapid test devices are commercially available to FPT testing from Midland BioProducts Corporation, Boone, Iowa 50036 U.S.A. These devices are manufactured and labeled for use with bovine blood samples. In the assay device, the presence of bovine IgG in the sample at 10 mg/mL or higher will inhibit the appearance of a colored line at the "T" location of the cassette. Conversely, IgG at a concentration in the sample of lower than 10 mg/mL will not inhibit the presence of the line which can be seen by eye. Oral fluid samples obtained and prepared as described in Example I were tested using these devices using both the procedure recommended by the manufacturer and a method specially modified by the inventor in order to obtain readable results with IgG concentrations lower than those expected in calf blood such as those of neonatal bovine saliva. When tested using the manufacturer's procedure, no inhibition of the indicator line formation was observed. These results were expected based on the ELISA results presented in Example IV. The special modified procedure involved applying 50 µL of sample into the sample well followed by the addition of 200 µL of diluent supplied with the tests. Three oral fluid samples were testing in this manner obtained from: a adult dairy cow, a bull calf 24 hours old, and calf No. 505 9 days old. The cow sample was found to be negative for IgG and both calf samples were positive for IgG. A photograph of the devices used is shown in FIG. 1. These results support the findings described in previous Examples that IgG is surprisingly present in calf oral fluid in higher concentration than that found in adult cows. In addition, these results indicate that specially designed rapid tests of lateral flow mechanism would prove useful in practicing the present invention to give on-site results in ungulate neonatal animals.

EXAMPLE VII

Detection and Measurement of IgA in Neonatal Oral Fluid

Oral fluid samples were collected and tested for IgA by ELISA as described in previous examples. Even prior to feeding calf oral fluid had concentrations of IgA at least 10 µg/mL and more typically at least 30 µg/mL. These are higher than those of IgG in the same samples. Upon feeding IgA concentrations generally increased slightly and not as much either relatively or absolutely as those of IgG. The comparison between IgG and IgA concentration at time 0 and 24 hours postpartum is shown in Table 4, which include data selected from those presented in Table 2 and 3 to show the comparison of changes in IgG and IgA in neonatal bovine oral fluid over time. Amounts of IgG & IgA as determined by ELISA are shown as µg/mL. As can be seen from Table 4, whereas the mean concentration of IgG went from 9 to 78 µg/mL during the first day of life, an almost nine-fold increase, in the same samples from the same animals IgA concentrations went from 30 to 34 µg/mL, roughly a 13% increase. These findings are very significant when the fact that immunoglobulins secreted into oral fluid are lost from the blood and must be replaced in the

TABLE 4

| | Time Post-Partum, Hrs Immunoglobulin Concentration | | | |
|---|---|---|---|---|
| | IgG | | IgA | |
| Animal ID | 0 | 24 | 0 | 24 |
| Bull 33 | 1 | 114 | 47 | 51 |
| Heifer 504 | 4 | 134 | 37 | 41 |
| Bull 29 | 8 | 74 | 36 | 41 |
| Bull 30 | 10 | 43 | 15 | 36 |
| Bull 1 | 11 | 137 | 34 | 43 |
| Bull 19 | 11 | 57 | 14 | 38 |
| Bull 32 | 11 | 21 | 44 | 7 |
| Mean = | 9 | 78 | 30 | 34 |
| Std Dev = | 2 | 44 | 13 | 15 | circulation as oral fluid is swallowed or otherwise lost from the animal. Even if the oral fluid immunoglobulin is resorbed by the same mechanism that transfer immunoglobulins from colostrum to the neonatal animal, such recover would likely at best result in maintaining the level of immunoglobulin, not increasing them. As in previous examples, the conclusion to be drawn from these results is that oral fluid testing is a valuable tool in evaluating the immune status of neonatal ungulates.

EXAMPLE VIII

Detection and Measurement of IgG, IgG1, and IgA in Neonatal Serum Samples by ELISA Serum samples collected as described previously from seven (7) calves at various times after birth including prior to the calves receiving any postpartum nutrition, a sample herein denoted as time 0. At time 0, the mean serum concentration of IgG, IgG1, and IgA was determined to be 310, 17, and equal to or less than 1 µg/mL respectively. This IgG result is consistent with findings presented previously herein that time 0 SRID for these samples showed less than detectable levels of serum IgG.

Serum was collected from these same calves 24 hours later during which time they had received more than one feeding. The IgG, IgG1, and IgA concentrations were found to be 35,000; 3,300; and 8000 µg/mL respectively. As was found with oral fluid testing results, the concentration of IgG increased significantly between pre-feeding and post-feeding in the animals. In both cases the results are consistent with those expected as a result of transfer of immunoglobulins to neonatal ungulates by feeding. Thus, the foregoing data demonstrate that the instant invention provides valuable information that is useful in assessing passive transfer of immunity.

EXAMPLE IX

Detection and Measurement of IgG in Foal Oral Fluid by ELISA

Oral fluid samples were collected from neonatal quarter horse foals and were tested using commercially available ELISA kits for IgG concentration. The foals used in this study were permitted to suckle their dams. Prior to ingesting colostrum the concentration of IgG was typically less than 10 µg/mL of sample. After feeding, the concentration of IgG in oral fluid was found to be greater than that prior to feeding and most frequently greater than 20 µg/mL. These data indicate that IgG is present in neonatal oral fluid at concentrations sufficiently high to be detected and measured and, therefore, useful in monitoring the transfer of immunity in neonatal horses. In addition, these data indicate that IgG rapidly appears in oral fluid of neonatal foals. This finding is surprising in light of the normal prevalence of IgA in saliva and oral fluid of ungulates. The data of this Example when taken in combination with those presented in other Examples presented herein give evidence that ingested immunoglobulins are secreted in oral fluid in neonatal animals of two distinct taxonomic Orders of ungulates: Artiodactyla to which the cattle (Bovidae) belong and Perissodactyla to which horses (Equidae) belong. These two species are ungulates and therefore have similar placental structures. As a result the two species provide passive transfer similarly despite sufficiently significant differences to classify them in different Orders.

I claim:

1. A method for determining immunoglobulins in a neonatal ungulate comprising obtaining a sample of oral secretions from the neonatal ungulate and measuring an amount of total immunoglobulins or total immunoglobulin type or subtype in the sample of oral secretions, wherein the sample of oral secretions is obtained from the neonatal ungulate not more than 48 hours after birth of the neonatal ungulate.

2. The method of claim 1, wherein the neonatal ungulate is a member of a taxonomical grouping selected from Bodivae, Equidae, Cervidae and Suidae.

3. The method of claim 1, wherein the neonatal ungulate is a member of the Order Artiodactyla or Perissodactyla.

4. The method of claim 3, wherein the member of Artiodactyla is a *Bos taurus* or *Bos primigenius*.

5. The method of claim 1, wherein the sample of oral secretions is obtained from the neonatal ungulate not more than 18 hours after birth of the neonatal ungulate.

6. The method of claim 1, wherein the sample of oral secretions is obtained from the neonatal ungulate not more than 12 hours after birth of the neonatal ungulate.

7. The method of claim 1, wherein a concentration of IgG is measured in the sample of oral secretions.

8. The method of claim 1, subsequent to obtaining the sample of oral secretions, further comprising obtaining a second sample of oral secretions from the neonatal ungulate and measuring immunoglobulins in the second sample of oral secretions.

9. The method of claim 8, wherein the second sample of oral secretions is taken at a period of from 1 hour to ten days subsequent to obtaining the sample of oral secretions.

10. The method of claim 1, further comprising communicating the amount of the total immunoglobulins or the total immunoglobulin type or subtype measured in the sample of oral secretions to an animal health care provider.

11. The method of claim 1, wherein determining the amount of the total immunoglobulins or the total immunoglobulin type or subtype that is lower than a control is indicative that the neonatal ungulate is in need of supplementation with a composition comprising immunoglobulins.

12. The method of claim 1, wherein the amount of immunoglobulins that is lower the control is an amount of IgG.

13. The method of claim 11, further comprising administering the composition comprising immunoglobulins to the neonatal ungulate.

\* \* \* \* \*